United States Patent [19]

McLaughlin et al.

[11] Patent Number: 5,312,409
[45] Date of Patent: May 17, 1994

[54] DRILL ALIGNMENT GUIDE

[76] Inventors: Robert E. McLaughlin; Gwo-Jaw Wang, both of Department of Orthopaedics and Rehabilitation University of Va. Medical Center, P.O. Box 159; Colin McLaurin, Department of Rehab. Engineering, University of Virginia Medical Center, P.O. Box 346, all of Charlottesville, Va. 22908

[21] Appl. No.: 890,780
[22] Filed: Jun. 1, 1992
[51] Int. Cl.⁵ .................. A61F 5/00; A61F 2/32
[52] U.S. Cl. ............................. 606/86; 606/96
[58] Field of Search .............. 606/96, 97, 98, 87, 606/105, 80, 86, 88

[56]  References Cited

U.S. PATENT DOCUMENTS

| | | | |
|---|---|---|---|
| 1,635,137 | 7/1927 | Mullens | 606/86 |
| 2,181,746 | 11/1939 | Siebrandt | 606/96 |
| 3,945,377 | 3/1976 | Kronner | 606/96 |
| 3,964,738 | 6/1976 | Owen | 296/236 |
| 4,235,428 | 11/1980 | Davis | 606/96 |
| 4,655,218 | 4/1987 | Kulik | 606/86 |
| 4,896,663 | 1/1990 | Vandewalls | 606/80 |
| 5,002,547 | 3/1991 | Poggie | 606/96 |
| 5,047,032 | 9/1991 | Jellicoe | 606/87 |
| 5,108,401 | 4/1992 | Insall | 606/87 |
| 5,129,908 | 7/1992 | Petersen | 606/86 |

FOREIGN PATENT DOCUMENTS

| | | | |
|---|---|---|---|
| 0350780 | 1/1990 | European Pat. Off. | 606/96 |
| 0482268 | 3/1938 | United Kingdom | 606/96 |

Primary Examiner—Michael A. Brown
Attorney, Agent, or Firm—Sughrue, Mion, Zinn, Macpeak & Seas

[57]  ABSTRACT

An alignment apparatus for guiding a cutting element along a predetermined path, the apparatus including a frame for guiding the cutting element along the predetermined path; and an adjustable clamp assembly, connected to the frame, for clamping a bone such that an intramedullary canal of the clamped bone is disposed along the predetermined path.

12 Claims, 3 Drawing Sheets

DRILL ALIGNMENT GUIDE

FIELD OF THE INVENTION

The present invention relates to a drill alignment guide, and, more particularly, to a drill alignment guide for use in, for example, removing cement from the medullary channel of a femur.

BACKGROUND OF THE INVENTION

In hip replacement surgery, a prosthesis is connected to the femur via cement or other adhesive material provided in the femoral canal. In hip replacement surgery in which a previously insert prosthesis is replaced (e.g., because the cement or adhesive has become weak), it is necessary to remove at least a part of the original cement or adhesive from the femoral canal. Loose fragments of the original cement or adhesive must be completely removed. Accordingly, at least some rechannelization of the femoral canal is necessary, and at least some reaming out of the old cement or adhesive is necessary to accommodate the new prosthesis. When reaming out the old cement or adhesive, it is essential that no damage be done to the canal or femoral shaft, since perforations may prevent adequate fixation of the new prosthesis or weaken the femur. Consequently, during the reaming operation, a guide device is needed so that the drill or other cutting element does not deviate from the drilling or cutting path, thereby preventing perforation or other trauma to the bone.

The following are examples of different alignment devices known in the art.

U.S. Pat. No. 4,860,737 to Davey et al discloses a drill alignment apparatus which includes a housing handle having a drill shaft which extends therefrom along an axis, an alignment rod which is parallel to the drill shaft, and an alignment rod support which is connected between one end of the alignment rod and the housing handle. The Davey et al apparatus further includes a clamp having apertures for receiving the alignment rod. The clamp further includes "tines" for engaging the femur.

As indicated above, Davey et al discloses the use of "tines" for engaging the femur, and also discloses that a set or inventory tines be provided to accommodate various bone sizes. The "tines" disclosed in Davey et al correspond to a plate or a set of plates each having tines separated by varying distances. In this regard, the Davey et al apparatus is similar to the so-called "Charnley guide". In Davey et al, the tines of the set of plates vary to accommodate varying widths of bones. However, two disadvantages are attendant with the Davey et al and the so-called "Charnely guide". First, a relatively large inventory of different-sized plates are required in order to accommodate the various sizes of bones. Second, while a plate can be selected from the inventory of different plates for a particular bone, the selected plate usually does not provide a tight grip of the bone, thereby requiring the surgeon to constantly hold the plate against the bone so that the dill bit does not slip off of the bone or bounce off the hard cement and perforate softer surrounding bone.

Great Britain Patent No. 1,448,111 to Crabbe discloses a device for fixing bone fractures. Specifically, Crabbe discloses a device used to guide a pin for neck fractures of the femur. The device includes an L-shaped rod or tube having a sleeve for receiving a tubular shaft and a clamp having an arcuate section adapted to engage the head of a femoral neck. The Crabbe device is not suited to guide a drill to ream out the medullary canal or shaft.

U.S. Pat. No. 4,896,663 to Vandewalls discloses a femoral drill jig including a clamping mechanism including an operating arm, and a cross beam. The jig is used to center a cup over the ball of the femur, which is a procedure seldom used anymore.

U.S. Pat. No. 4,364,381 to Sher et al discloses a surgical clamp and drill-guide instrument including a C-clamp having a curved lower portion, an upright post, and an upper vice arm which extends from a central body portion located on the upright post. The instrument is used exclusively in the jaw for postioning dental implants.

U.S. Pat. Nos. 2,181,746 and 3,945,377 disclose bone clamps/drill guide devices which employ scissor-like clamps.

U.S. Pat. No. 4,502,475 to Weigle et al discloses a drill guide and clamping apparatus including an adjustable scissor-like assembly. The apparatus is used to align screw holes in plates used to fix broken fractured bones.

SUMMARY OF THE INVENTION

It is an object of the present invention to provide a drill alignment guide which firmly clamps the bone for a drilling operation.

It is another object of the present invention to provide a drill alignment guide which includes an adjustable clamp to accommodate bones of different sizes.

It is another object of the invention to provide a drill alignment guide which does not require an inventory of various clamping devices.

It is still another object of the invention to provide a drill alignment guide which can accommodate various sizes of drill bits.

It is still another object of the invention to provide a drill alignment guide having a clamp assembly which can be easily manipulated.

These and other objects are accomplished by the drill alignment guide apparatus of the present invention which guides a drill bit or other cutting element along a predetermined path. The apparatus includes a frame for guiding the cutting element along the predetermined path; and an adjustable clamp assembly, connected to the frame, for firmly clamping a bone such that an intramedullary canal of the clamped bone is disposed along the predetermined path fo the cutting element.

DETAILED DESCRIPTION OF A PREFERRED EMBODIMENT

Figure 1:
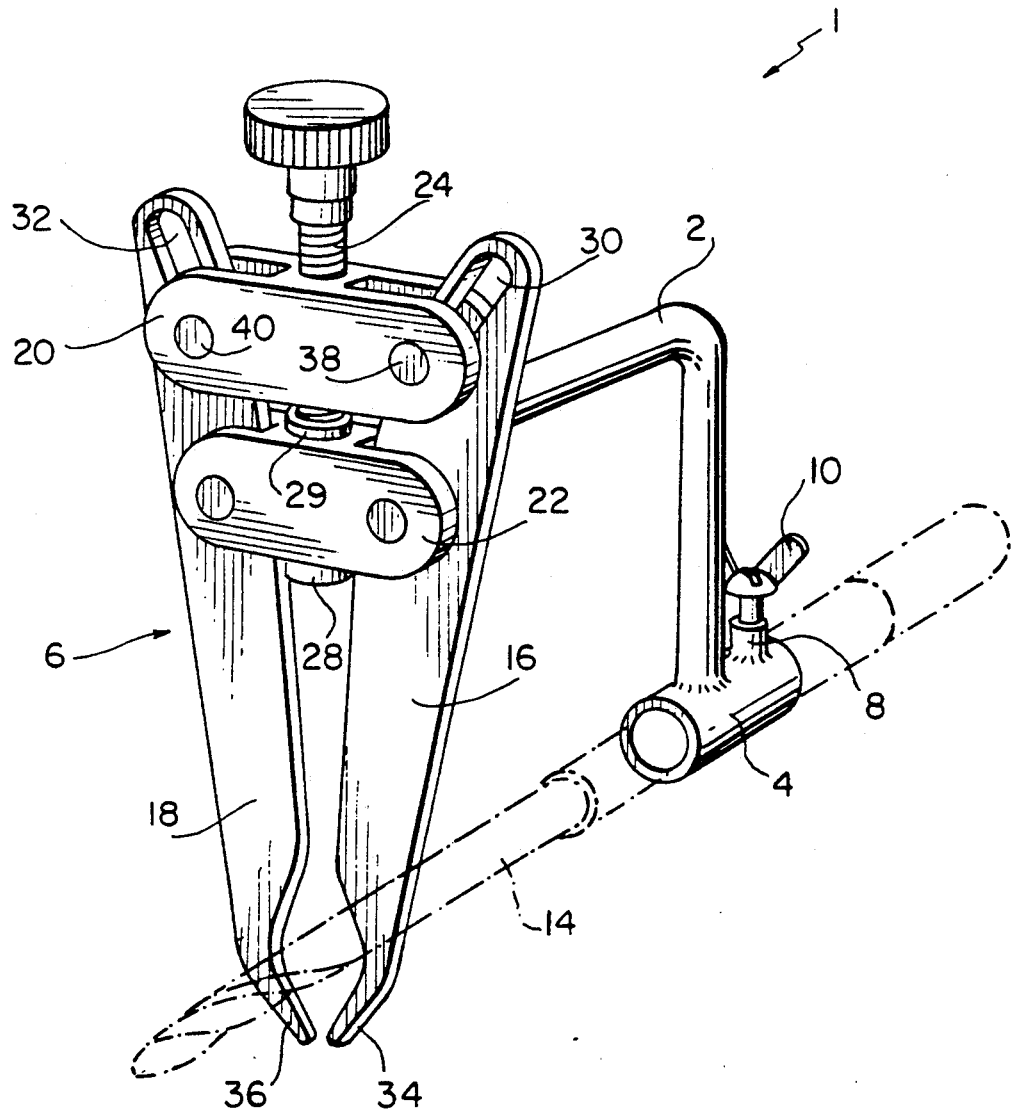
FIG. 1 is a perspective view of the drill alignment guide according to the invention.
Figure 2:
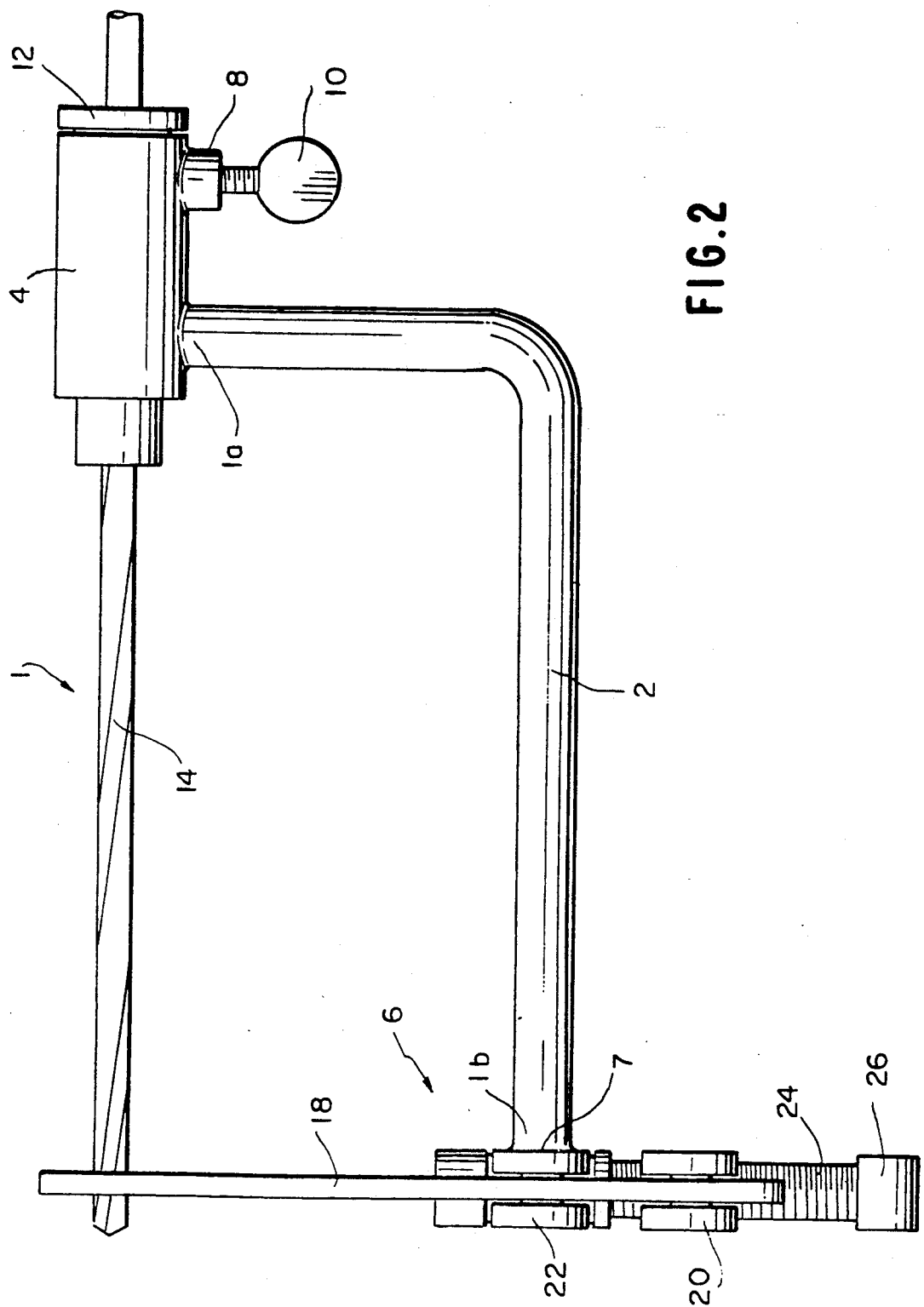
FIG. 2 is a side view of the drill alignment guide shown in FIG. 1.

FIG. 1 is a perspective view of the drill alignment guide apparatus according to a preferred embodiment of the invention. FIG. 2 is a side view of the drill alignment guide apparatus shown in FIG. 1. As shown in FIGS. 1 and 2, the drill alignment guide apparatus 1 comprises a frame including an L-shaped bar 2 and a tubular drill guide 4. The femur drill jig 1 also includes a clamp assembly 6. One end 1a of the L-shaped bar 2 is welded to the drill guide 4, and the other end 1b of the L-shaped bar 2 is welded to a frame attachment point 7 of the clamp assembly 6.

As shown in FIG. 2, the drill guide 4 includes a port 8 for receiving a set screw 10 which may be, for example, a wing screw, a thumb screw or the like. The set screw 10 serves to fix or set a drill guide bushing 12 within the drill guide 4. A drill bit 14 is slidingly received in the internal longitudinal bore of the drill guide bushing 12 after bushing 12 has been set or fixed by set screw 10. The drill guide bushing 12 may be of different sizes shapes depending on the size and shape of the particular drill bit 14 being used in the surgical operation.

Figure 3:
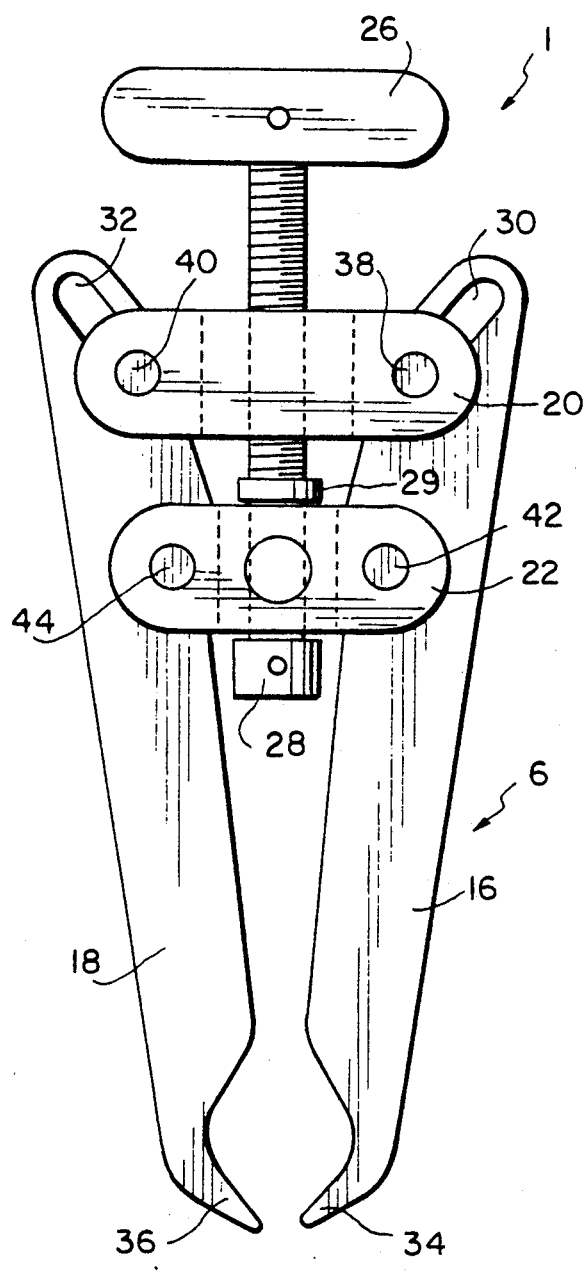
FIG. 3 is a front view of the clamp assembly of the drill alignment guide of FIGS. 1-2.
Figure 4:
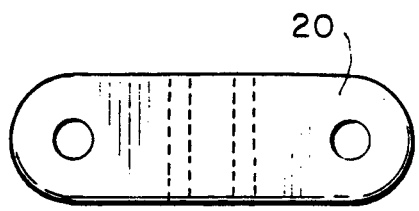
FIG. 4 is a front view of the cam follower according to the invention.
Figure 5:
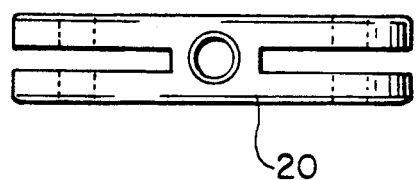
FIG. 5 is a side view of the cam follower shown in FIG. 4.

FIG. 3 shows the clamp assembly 6 in more detail. As shown in FIG. 3, the clamp assembly 6 includes a pair of jaws 16 and 18, a cam follower 20, a pivot 22, a threaded screw shaft 24, a wing nut 26, and screw shaft retaining collars 28 and 29. The jaws 16 and 18 include respective slots 30, 32 at one end thereof, and also include respective in-turned ends 34, 36 at the other ends thereof. As shown in FIGS. 3-5, the cam follower 20 includes a pair of openings for receiving pins 38, 40. Each of the pins 38 and 40 has a shape which corresponds to the shape of slots 30 and 32 of jaws 16 and 18, respectively. The cam follower 20 also includes a threaded center hole for receiving the threaded screw shaft 24.

Figure 6:
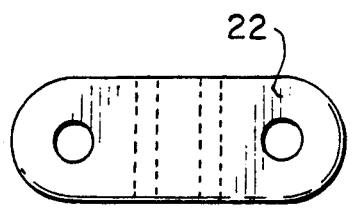
FIG. 6 is a front view of the pivot according to the invention.
Figure 7:
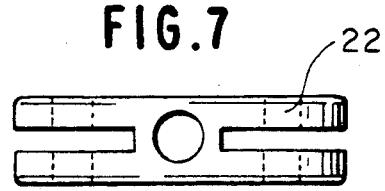
FIG. 7 is a side view of the pivot shown in FIG. 6.

As shown in FIGS. 3 and 6-7, the pivot 22 includes a pair of openings for receiving the pair of pins 42 and 44, along with a non-threaded center hole for receiving the screw shaft 24. As indicated above in connection with FIG. 2, the pivot 22 is connected to one end 1b of L-shaped bar 2 at the frame attachment point 7.

As best seen in FIG. 2, the screw shaft 24 extends through the threaded center hole of cam follower 20 and through the non-threaded center hole of pivot 22. One end of the screw shaft 24 is connected to the wing nut 26 which upon rotation thereof causes the screw shaft 24 to rotate. The other end of the screw shaft 24 is connected to the retaining collar or washer 28.

The operation of the clamp assembly 6 will now be described in conjunction with FIG. 3.

In FIG. 3, the clamp assembly 6 has been operated so as to provide the narrowest possible opening between the in-turned ends 34 and 36 of jaws 16 and 18, respectively. In this position of the clamp assembly 6 (i.e., the position shown in FIG. 3), the pins 38 and 40 of the cam follower 20 are disposed at those ends of the slots 30, 32 which are farthest from the wing nut 26. In order to widen the opening between the in-turned ends 34 and 36 of clamp assembly 6, the wing nut 26 is rotated, thereby causing the screw shaft 24 to rotate. Since the threaded center hole of cam follower 20 receives the screw shaft 24, and since pins 38 and 40 of the cam follower 20 are disposed in slots 30, 32, rotation of the screw shaft 24 will cause the pins 38, 40 of cam follower 20 to "follow" the slots 30, 32, respectively, thereby causing cam follower 20 to move away from the pivot 22 and towards wing nut 26. As the cam follower 20 moves away from pivot 22 (i.e., pins 38, 40 move along slots 30, 32, respectively), the jaws 16 and 18 will pivot about pins 44 and 46, respectively, thereby causing the jaws 16 and 18 to move away from each other. As a result, the opening between in-turned ends 34 and 36 will widen. The widest possible opening between the in-turned ends 34, 36 is provided when pins 38, 40 are disposed at those respective ends of slots 30, 32 which are closest to the wing nut 26.

The clamp assembly 6 may be operated to provide the widest and narrowest openings between in-turned ends 34, 36 as described above, or may be operated to provide an intermediate opening which is between the widest and narrowest openings.

The operation of the femur drill jig will now be described.

Initially, the clamp assembly 6 is operated in the manner described above such that the in-turned ends 34, 36 of jaws 16, 18, respectively, are positioned so as to provide the widest possible opening therebetween, or the clamp assembly 6 is operated such that an intermediate opening between the in-turned ends 34, 36 is at least greater than the diameter of the femur. The clamp assembly 6 is then positioned on the femur at about six or eight inches from the proximal end thereof. The wing nut 6 is then rotated so as to rotate the screw shaft 24 and move the cam follower 20 down the screw shaft 24, thereby moving the jaws 16 and 18 towards each other. The rotation of the wing nut 6 is continued until the jaws 16 and 18 firmly clamp the femur therebetween.

Referring to FIGS. 1 and 2, the drill guide 4 is disposed relative to the clamp assembly 6 such that when the clamp assembly 6 is firmly clamped onto the femur, the center longitudinal axis of the drill guide 4 is aligned with the axis extending through the center of the opening between the in-turned ends 34, 36 of the jaws 16, 18, respectively. Consequently, when the drill bit 14 is inserted in the drill busing 12 of the drill guide 4, the longitudinal axis of the drill bit 14 will coincide with the center longitudinal axis of the femur. Once the drill bit 14 is properly aligned in this manner, the surgeon may activate the drill (not shown) and commence the drilling procedure. As the drill bit 14 is directed into the intermedullary canal of the femur, it is maintained on a drill path which substantially coincides with the center longitudinal axis of the intermedullary canal of the femur due to the interaction of frame 2, drill guide 4 and clamp assembly 6. Since the clamp assembly 6 is firmly clamped onto the femur, it is not necessary for the surgeon to hold the clamp assembly 6 during the drilling operation.

The drill alignment guide may be manufactured from stainless steel or other suitable materials.

Although a particular embodiment of the invention has been described and shown, it is understood that modifications and variations may readily occur to those skilled in the art. For example, while the particular embodiment has been described in connection with re-channelization of a femur, those skilled in the art will understand that the invention may be applied to various different surgical operations. Consequently, it is intended that the claims be interpreted to cover such modifications and equivalents.

What is claimed is:

1. An alignment apparatus for guiding a cutting element along a predetermined path, said apparatus comprising:
   means for removing cement from an intramedullary canal of a bone, said means comprising:
   a frame for guiding the cutting element along the predetermined path,
   an adjustable clamp assembly, connected to said frame, for clamping the bone such that the intramedullary canal of the clamped bone is disposed along the predetermined path, said adjustable clamp assembly including a pair of pivotable jaws having a pair of slots, respectively, and a cam follower connected to the slots of said pivotable jaws, wherein the slot of each of said pair of pivotable jaws is disposed at one end thereof.

2. The alignment apparatus as defined in claim 1, wherein said frame comprises a guide for guiding the cutting element, and an L-shaped bar, and wherein one end of said L-shaped bar is connected to said guide, and wherein the other end of said L-shaped bar is connected to said adjustable clamp assembly.

3. The alignment apparatus as defined in claim 1, wherein said guide includes a port for receiving a screw.

4. The alignment apparatus as defined in claim 1, further comprising a pivot, and wherein each of said pivotable jaws is connected to said pivot.

5. The alignment apparatus as defined in claim 4, wherein said pivot includes a pair of pins, and wherein said pair of jaws are pivotable about the pair of pins of said pivot, respectively.

6. The alignment apparatus as defined in claim 4, wherein said cam follower includes a threaded center hole, and said pivot includes a non-threaded center hole, and wherein the apparatus further comprises a screw shaft disposed through the threaded center hole of said cam follower and through said non-threaded center hole of said pivot.

7. The alignment apparatus as defined in claim 4, further comprising a wing nut connected to one end of said wing nut shaft such that rotation of said screw causes rotation of said screw shaft.

8. The alignment apparatus as defined in claim 1, wherein said cam follower includes a pair of pins, and wherein each of said pins is disposed through a different one of the slots of said jaws.

9. The drill alignment apparatus as defined in claim 1, wherein said adjustable clamp assembly further includes a pivot, and wherein each of said pivotable jaws is pivotable about said pivot.

10. The drill alignment apparatus as defined in claim 9, wherein said cam follower includes a threaded center hole, said pivot includes a non-threaded center hole, and wherein said adjustable clamp assembly further includes a screw shaft disposed through said threaded center hole of said cam follower and through said non-threaded center hole of said pivot.

11. The drill alignment apparatus as defined in claim 9, wherein said adjustable clamp assembly further includes a handle which is connected to one end of said said screw shaft such that rotation of said handle causes rotation of said screw shaft.

12. A drill alignment apparatus for guiding a drill bit along a predetermined path, said apparatus comprising:
   means for removing cement from an intramedullary canal of a bone, said means comprising:
   a frame of guiding the drill bit along the predetermined path, said frame comprising a drill bit guide and an L-shaped bar having one end thereof integrally attached to said drill bit guide; and
   an adjustable clamp assembly, integrally connected to the other end of said L-shaped bar, for clamping the bone such that the intramedullary canal of the clamped bone is disposed along the predetermined path, wherein said adjustable clamp assembly includes a pair of pivotable jaws each of which has a slot at an end thereof, and wherein said adjustable clamp assembly further includes a cam follower connected to the slots of said pivotable jaws.

* * * * *